United States Patent [19]

Weinschenk, III et al.

[11] Patent Number: 5,359,021

[45] Date of Patent: Oct. 25, 1994

[54] POLYMERIC COMPOSITIONS AND INTRAOCULAR LENSES MADE FROM SAME

[75] Inventors: Joseph I. Weinschenk, III; F. Richard Christ, both of Laguna Beach, Calif.

[73] Assignee: Allergan, Inc., Irvine, Calif.

[21] Appl. No.: 123,016

[22] Filed: Sep. 16, 1993

Related U.S. Application Data

[62] Division of Ser. No. 973,470, Nov. 9, 1992.

[51] Int. Cl.$^5$ .................. C08F 226/10; C08F 220/54; C08F 220/10; C08F 212/08; A61F 2/16
[52] U.S. Cl. .................. 526/264; 526/303.1; 526/328.5; 526/347; 623/6
[58] Field of Search .................. 526/264, 303.1, 328.5, 526/347; 623/6

[56] References Cited

U.S. PATENT DOCUMENTS

| | | | |
|---|---|---|---|
| 4,834,750 | 5/1989 | Gupta | 623/6 |
| 4,834,753 | 5/1989 | Sulc et al. | 623/6 |
| 4,916,197 | 4/1990 | Vacik et al. | 526/264 |
| 5,147,394 | 9/1992 | Siepser et al. | 623/6 |

FOREIGN PATENT DOCUMENTS

| | | |
|---|---|---|
| 0308130 | 3/1989 | European Pat. Off. . |
| 0485197 | 5/1992 | European Pat. Off. . |
| 0492126 | 7/1992 | European Pat. Off. . |

OTHER PUBLICATIONS

Acrylens TM A Technical Evaluation Of Foldable Intraocular Lenses, 1990 Loptex Research Inc. Data Sheet.
Abstract 19–6, Fluoro Acrylic Fluoroalkyl Methacrylate Yoshida et al.
Abstract:Nonhydrophilic flexible intraocular lens materials having high strength. JP 62097559 A2 7 May 1987, Showa, 7 pp. (Japan).

*Primary Examiner*—Joseph L. Schofer
*Assistant Examiner*—Wu C. Cheng
*Attorney, Agent, or Firm*—Gordon L. Peterson; Frank J. Uxa, Jr.

[57] ABSTRACT

New high refractive index polymeric compositions and foldable intraocular lenses made from such compositions are disclosed. In one embodiment, the present compositions comprise a copolymer including a major amount of a first constituent derived from a first monomeric component the homopolymers of which have a refractive index of at least about 1.50, a minor amount of a second constituent derived from a second monomeric component other than the first monomeric component the homopolymers of which have a glass transition temperature of less than about 30° C., preferably less than about 22° C., and a third constituent derived from a crosslinking monomeric component in an amount effective to facilitate returning a deformed intraocular lens made of the composition to its original shape.

19 Claims, 1 Drawing Sheet

POLYMERIC COMPOSITIONS AND INTRAOCULAR LENSES MADE FROM SAME

This application is a division of application Ser. No. 973,470 pending, filed Nov. 9, 1992.

BACKGROUND OF THE INVENTION

The present invention relates to polymeric compositions and to intraocular lenses made from such compositions. More particularly, the invention relates to polymeric compositions which have high refractive indexes and to intraocular lenses, preferably deformable intraocular lenses, made therefrom.

Intraocular lenses (IOLs) have been known for a long time, since shortly after the end of World War II. Such a lens is surgically implanted into a mammalian eye, e.g., human eye, to replace a damaged or diseased natural lens of the eye and restore the patient's vision.

Although IOLs are made from "hard" or "rigid" polymeric or glass optical materials, such as polymethylmethacrylate (which has a refractive index of 1.48), soft resilient polymeric materials, such as silicones, have been increasingly used, for the reasons discussed below, in ophthalmic applications.

Since soft IOLs are deformable, for example, foldable or rollable, for implantation, a smaller incision can be surgically cut in the eye than for the implantation of "hard" IOLs of the same optical power. The smaller the incision, the less trauma the patient's eye experiences and the faster post-operative healing occurs. An incision of about 3 mm is ideal since this size incision is presently required to remove the natural lens after it has been broken up, for example, emulsified in a conventional phacoemulsification procedure. In contrast the typical IOL optic has a diameter of about 6 mm.

The size and mechanical characteristics of the deformable IOLs play an important role. As is well understood by those skilled in the art, for successful implantation, the deformable IOL must have sufficient structural integrity, elasticity and elongation and be small enough in size to permit deforming for insertion through a small incision. After insertion, the lens must, of course, regain its original shape and have sufficient structural integrity to retain such shape under normal use conditions.

In general, the thinner the deformable IOL the smaller the incision in the eye that is required. On the other hand, in order to function optically as an IOL, the lens must have sufficient optical refractory power. Also, the higher the optical refractive index of the material making up the IOL, the thinner the IOL can be and still obtain the same optical refractory power.

IOLs made of silicone polymeric materials conventionally have refractive indexes which are no greater than about 1.46. Consequently, their center thicknesses are substantially greater than those of IOLs composed of materials having higher refractive indexes. Deformable IOLs made of acrylic materials can be too rigid for use at room temperature, which rigidity can result in cracking if the IOL is folded quickly; can be near silicone polymeric materials in refractive index; or can be quite tacky in nature, which tackiness inhibits deforming to a sufficiently small size for insertion through a very small incision and may cause handling problems.

Gupta U.S. Pat. No. 4,834,750 discloses IOLs with optics made of copolymers of methacrylate esters which form homopolymers that are relatively hard at room temperature and acrylate esters which form homopolymers that are relatively soft at room temperature. Such copolymers are crosslinked with a diacrylate ester to produce an acrylic material having a tack-free surface and a glass transition temperature in the range of −30° to 25° C. This patent discloses that such optics can be deformed for insertion into the eye. However, this patent is silent on the refractive index of IOL optics and is, thus, unconcerned with forming deformable IOLs with high refractive indexes. For example, none of the specific monomers disclosed in this patent provide homopolymers which have a refractive index of at least about 1.50.

It would be advantageous to provide an IOL material of construction which has good optical properties, including optical clarity and high refractive index, and has sufficient characteristics and properties to provide an IOL which is effectively deformable for insertion through a small incision.

SUMMARY OF THE INVENTION

New polymeric materials and IOLs produced from such polymeric materials have been discovered by the present inventors. The present polymeric materials are derived from a combination of monomers and provide very useful optical properties in terms of optical clarity and high refractive index, and can be formed into IOLs which are effectively deformable, preferably foldable, for insertion through small surgical incisions, preferably on the order of about 3 mm or less (in maximum transverse dimension). Moreover, the present IOLs regain their original shape in a reasonable period of time at conditions present in the eye. The present polymeric materials can be produced using conventional monomeric components and conventional techniques, e.g., conventional polymerization techniques. Thus, the present invention is very effective and easy to practice and results in polymeric materials and IOLs which have outstanding properties.

In one broad aspect, the present invention relates to compositions which comprise a copolymer including a first constituent, a second constituent and a third constituent. The first constituent is derived from a monomeric component the homopolymers of which have a refractive index of at least about 1.50, which is a higher refractive index than methyl methacrylate homopolymer. The homopolymers of such first monomeric component are preferably rigid. The second constituent is derived from a monomeric component, other than the monomeric component from which the first constituent is derived, the homopolymers of which have a glass transition temperature of less than about 30° C., preferably less than about 22° C. The third constituent is derived from a cross-linking monomeric component and is present in an amount effective to facilitate returning a deformed IOL (deformed for implantation) made from the composition to its original shape, for example, at the conditions present in the human eye.

In another broad aspect of the present invention, IOLs are provided which are sized and adapted to be inserted, preferably in a deformed state, through an incision, preferably an incision of about 3 mm, into a mammalian eye for use. The IOLs of the present invention comprise the compositions, as described herein.

These and other aspects of the present invention are set forth in the following detailed description examples and claims, particularly when considered in conjunction with the accompanying drawings in which like parts bear like reference numerals.

DETAILED DESCRIPTION OF THE INVENTION

Figure 1:
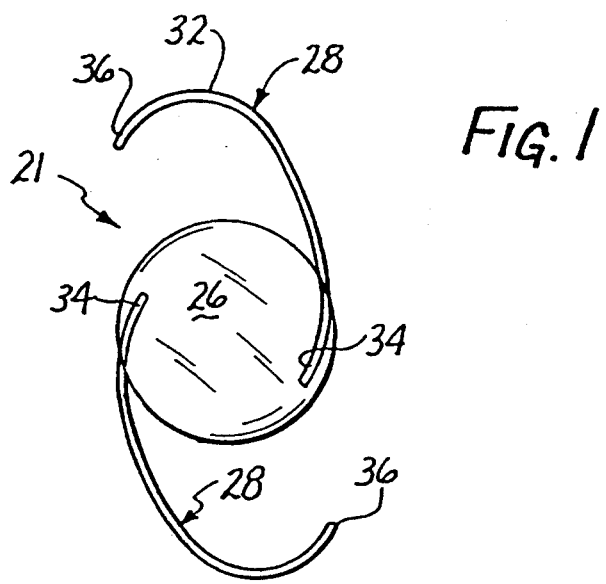
FIG. 1 is a plan view of an IOL in accordance with the present invention.

The present compositions comprise copolymers including at least three constituents. The first constituent, which is preferably present in the present copolymers in an amount of at least about 10% or about 20% by weight and more preferably in a major amount (at least about 50%) by weight, is derived from a first monomeric component the homopolymers of which have a refractive index of at least about 1.50, preferably at least about 1.52 or about 1.54. The homopolymers of the first monomeric component preferably have a substantial degree of rigidity. The second constituent, which is preferably present in the present copolymers in an amount of at least about 3% or about 10% or about 20% by weight, is derived from a second monomeric component other than the first monomeric component. Homopolymers of the second monomeric component have a glass transition temperature of less than about 30° C., preferably less than about 22° C.

The first and second constituents together are preferably at least about 80%, more preferably at least about 90%, by weight of the present copolymers. The first and second monomeric components are preferably selected so that each of these monomeric components can chemically react with the other monomeric component.

The third constituent of the present copolymers is derived from a cross-linking monomeric component, that is a monomeric component which can form cross-links in the present copolymers. This cross=linking monomeric component is preferably multi-functional and can chemically react with both the first and second monomeric components. The third constituent of the present copolymers is present in an amount effective to facilitate returning a deformed IOL made from the present composition to its original shape, for example, in a reasonable period of time, at the conditions present in the human eye.

The present copolymers are optically clear and have high refractive indexes, for example, at least about 1.50, and preferably at least about 1.52 or at least about 1.54. The combination of properties of the present copolymers, which allows the manufacture of effectively deformable IOLs having high optical power, is very advantageous.

As used herein, the term "homopolymer" refers to a polymer which is derived substantially completely from the monomeric component in question. Thus, such homopolymer includes as the primary, preferably sole, monomeric component, the monomeric component in question. Minor amounts of catalysts, initiators and the like may be included, as is conventionally the case, in order to facilitate the formation of the homopolymer. In addition, the homopolymers of both the first monomeric component and the second monomeric component have sufficiently high molecular weights or degrees of polymerization so as to be useful as IOL materials of construction.

The homopolymers of the first monomeric component are preferably rigid. An IOL made from such a "rigid" homopolymer is not deformable, for example, using systems which are specifically structured and used to deform IOLs for insertion through a small incision into the eye. The rigidity of the homopolymer of the first monomeric constituent may result in an IOL made from such homopolymer being not deformable, or breaking or otherwise deteriorating as a result of the application of force seeking to so deform such IOL for implantation through a small ocular incision.

The first constituent is preferably present in an amount of at least about 10% or at least about 20%, more preferably in a major amount, by weight of the present copolymers. The first monomeric component from which the first constituent is derived may be selected from compounds which meet the criteria set forth herein for such component. This monomeric component should be such as to provide the present copolymers with increased refractive index relative to the homopolymers of the second monomeric component. The homopolymers of the first monomeric component have a refractive index of at least about 1.50, preferably at least about 1.52 or at least about 1.54.

Of course, the first, second and third monomeric components should be such as to provide copolymers which are compatible for use in the eye, are optically clear and are otherwise suitable for use as materials of construction for IOLs. In one useful embodiment, each of the first, second and third monomeric components is substantially free of silicon, so that the resulting copolymer is not a silicone polymer. Each monomeric component useful in producing the present copolymers preferably includes at least one a functional group containing carbon-carbon unsaturation, more preferably a carbon-carbon double bond. The monomeric components may be substituted with substantially non- interfering substituents which have no substantial detrimental effect on the copolymer produced therefrom. Such substituents may include one or more elements, such as oxygen, nitrogen, carbon, hydrogen, halogen, sulfur phosphorus, and the like and mixtures and combinations thereof.

Particularly useful first monomeric components include styrene, vinyl carbazole, vinyl naphthalene, benzyl acrylate, phenyl acrylate, naphthyl acrylate, pentabromophenyl acrylate, 2-phenoxyethyl acrylate, 2-phenoxyethyl methacrylate, 2,3-dibromopropyl acrylate and mixtures thereof.

The second constituent is preferably present in an amount of at least about 2%, more preferably at least about 4% by weight of the copolymer. Any suitable second monomeric component which meets the criteria for such component set forth herein may be employed. Homopolymers of the second monomeric component have glass transition temperatures of less than about 30° C., preferably less than about 22° C. Particularly useful second monomeric components include n-butyl acrylate, n-hexyl acrylate, 2-ethylhexyl acrylate, 2-ethoxyethyl acrylate, 2,3-dibromopropyl acrylate, n-1, 1-dihydroperfluorobutyl acrylate and mixtures thereof.

The third or crosslinking monomeric component is often present in a minor amount relative to the amounts of the first and second monomeric components. Preferably, the third constituent is present in the copolymer in an amount of less than about 1% by weight of the copolymer. The third constituent of the present copolymers may be considered to be a crosslinker. The crosslinking monomeric component is often selected from multifunctional components, preferably able to chemically react with at least one functional group of each of the first monomeric component and the second monomeric component. The crosslinking monomeric component is chosen to be chemically reactible with at least one functional group associated with one or both of the first monomeric component and the second monomeric component. Examples of useful crosslinking monomeric components include ethylene glycol dimethacrylate, propylene glycol dimethacrylate, ethylene glycol diacrylate and the like and mixtures thereof.

In a particularly useful embodiment, the copolymers further include a fourth constituent derived from a hydrophilic monomeric component, other than the first, second and third monomeric components. This fourth constituent is present in an amount, preferably at least about 2% or about 4% by weight of the copolymer, effective to reduce the tackiness of the copolymer relative to a substantially identical copolymer without the fourth constituent. In addition, the presence of such a fourth constituent may provide one or more other benefits, e.g., enhanced tensile strength and enhanced compatibility with the environment in the eye, relative to a substantially identical copolymer without the fourth constituent. The fourth constituent is preferably present in an amount of less than about 15% by weight of the copolymer. Copolymers which include about 15% by weight or more of a constituent derived from hydrophilic monomeric components tend to form hydrogels when exposed to water., The present copolymers are preferably not hydrogel-forming. The advantageous properties of the present copolymers are preferably the result of selecting the proper constituents in accordance with the present invention rather than forming a hydrogel from such copolymers.

As used herein, the term "hydrophilic monomeric component" refers to compounds which produce hydrogel-forming homopolymers, that is homopolymers which become associated with substantial amounts for example at least about 20% based on the weight of the homopolymer, of water and which physically swell as a result of such Association. Specific examples of useful hydrophilic monomeric components include N-vinyl pyrrolidone; hydroxyalkyl acrylates and hydroxyalkyl methacrylates, such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl metharcylate, 2,3-dihydroxypropyl acrylate, 2,3 -dihydroxypropyl methacrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and mixtures thereof.

In one embodiment, the first monomeric component is characterized as including one or more aryl-containing groups. Without wishing to limit the present invention to any particular theory of operation, it is believed that the presence of such aryl-containing groups in the first monomeric component at least facilitates, and preferably leads to or results in, the present copolymers having desirably high refractive indexes. If the first monomeric component includes one or more aryl-containing groups, it is preferred that at least the second monomeric component, and more preferably that the second, third and fourth monomeric components, include no aryl-containing groups. It has been found that the specific first monomeric component selected, and the amount of such component used to form the copolymer, can effectively control the refractive index of the copolymer. In other words, the present copolymers are provided with desirably high refractive indexes without requiring that the second monomeric component, or the second, third and fourth monomeric components, have high refractive indexes comparable to the refractive index of the first monomeric component. This "single refractive index control" is very effective in achieving high refractive index copolymers, and allows flexibility in selecting the other monomeric component or components so that copolymers with advantageous properties, other than refractive index, for example, copolymers formable into IOLs which can be effectively deformed (for insertion) at room temperature, can be obtained.

The present copolymers may be produced using conventional polymerization techniques. For example, the monomers can be blended together and heated to an elevated temperature to facilitate the polymerization reaction. Catalysts and/or initiators, for example, selected from materials well known for such use in the polymerization art, may be included in the monomer mix in order to promote, and/or increase the rate of, the polymerization reaction. Examples of such initiators include 2,2'-azobis (2,4-dimethylpentanenitrile), 2,2'-azobis (2-methylpropanenitrile), 2,2'-azobis (2-methylbutanenitrile), peroxides such as benzoyl peroxide, UV initiators such as diethoxyacetophenone, and the like and mixtures thereof. In addition, effective amounts of ultraviolet light absorbing monomeric components, such as functional benzotriazole and benzophenone derivatives, may be included in the precursor monomer mix. Such UV light absorbing monomeric components are polymerized-into the final copolymer to provide the final copolymer with effective UV light absorbing properties.

In one particularly useful embodiment, the present copolymers are produced by mixing together the first monomeric component and the second monomeric component (and the fourth monomeric component, if any). This mixture is well blended, deareated and heated to a temperature, for example, of about 50° C. to about 80° C. and maintained at this temperature for a period of time, for example, of about 15 minutes to about 3 hours. The mixture undergoes partial polymerization to form a viscous liquid when cooled to about 25° C.

The final copolymer can be produced by combining this partially polymerized viscous liquid, the crosslinking monomeric component and catalyst and/or an initiator. Alternately, all the monomeric components and catalyst and/or initiator can be combined or mixed together. The viscous liquid, or monomeric mixture, is well blended, deareated and poured into a mold. The mold is heated, preferably to a temperature of about 40° C. to about 100° C., and the liquid or mixture is allowed to cure, preferably for about 1 hour to about 24 hours. The material in the mold is then post-cured, preferably at a temperature in the range of about 70° C. to about 130° C., for a period of time, preferably for about 2 to about 30 hours. After curing (and post-curing), the mold is disassembled and the molded optic recovered.

Alternately, the curing and post-curing occurs in a tube. The copolymer formed in the tube is cut into cylindrical lens blanks. The lens blanks can be machined to produce the finished optic. Such machining may involve milling and lathing at cryogenic temperatures.

Figure 2:
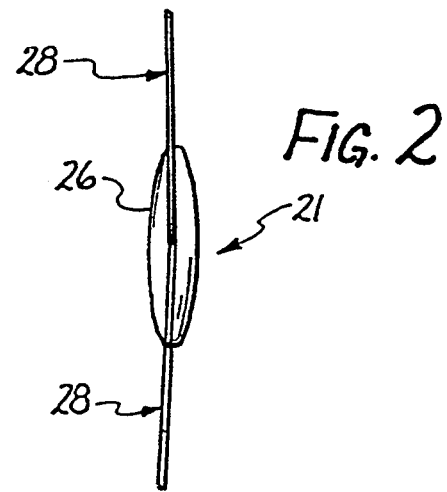
FIG. 2 is a side view of the IOL of FIG. 1.

Referring now to FIGS. 1 and 2, IOL 21 is illustrated as including a pair of radially outwardly extending haptics or fixation members 28 secured to optically clear optic 26. Each haptic 28 has a substantially uniform cross section throughout its length and is shown provided with a smoothly curved region 32, intermediate a lens bonding region 34 and a free end region 36. Although the illustrated embodiment is provided with two opposing haptics 28, it is understood that an IOL having only one haptic or more than two haptics bonded to the optic is within the scope of the invention.

Optic 26 is made of a copolymer in accordance with the present invention, for example, the copolymer as set forth in Example 1 hereof. Optic 26 can be formed in accordance with conventional IOL optic forming techniques, such as by injection molding and the like techniques. Alternately, the monomeric components can be first mixed in a tube and then cured in the tube. The resulting rod then is cut into buttons which are than cryolathed into IOL optics.

Typically, each haptic 28 comprises a flexible member comprising metal or, preferably, polymeric material, and having a substantially circular cross-section, although alternative cross-sectional configurations may be substituted, if desired. Although the haptics may take on any suitable configuration, the illustrated haptics 28 are relatively thin and flexible, while at the same time being sufficiently strong to provide support for IOL 21 in eye 10. The haptics 28 may comprise any of a variety of materials which exhibit sufficient supporting strength and resilience, and which are substantially biologically inert in the intended in vivo environment. Suitable materials for this purpose include, for example, polymeric materials such as polypropylene, polymethyl methacrylate, polycarbonates, polyamides, polyimides, polyacrylates, 2-hydroxymethylmethacrylate, poly (vinylidene fluoride) polytetrafluoroethylene and the like; and metals such as stainless steel, platinum, titanium, tantalum, shapememory alloys, e.g., nitonal, and the like. The haptics can be produced using conventional and well known forming techniques. For example, the preferred polymeric haptics can be formed in accordance with known thermoplastic polymer forming techniques, such as by injection molding or by extrusion.

The lens bonding regions 34 of the haptics 28, which, as described herein, are secured to Optic, may be provided with any of a variety of configurations, such as an anchoring loop, and anchoring "T", or other anchor structure, to provide a mechanical interlock with the optic, such as has been done in the prior art.

IOL 26 can be formed using any one of various techniques, such as those conventionally used to form IOLs. For example, the lens bonding regions 34 of haptics 28 can be placed in a mold which is filled with a mix of the monomeric components used to form the optic 26. The mold is then subjected to conditions, e.g., elevated temperature, effective to form the copolymer of the present invention from this monomer mix. The lens bonding regions 34 become bonded to the optic 26, thereby securing the haptics 28 to the optic. Alternately, the haptics 28 can be secured in recesses provided in the already formed optic 26.

Optic 26 has a refractive index of at least about 1.50, and is foldable for insertion into a human eye through an incision of about 3 mm in length. After insertion into the eye in the folded condition, IOL 21 returns to its original shape in a reasonable period of time, for example, on the order of about 3 seconds or about 20 seconds to about three minutes, and can be easily positioned in the eye for effective and long term use as a replacement for the natural lens normally present in the eye.

The following non-limiting examples illustrate certain aspects of the present invention.

EXAMPLE 1

The following formulation was blended, purged with nitrogen for 3 minutes and then cured into a crosslinked copolymer.

|  | Weight % |
| --- | --- |
| 2-phenoxyethyl acrylate | 89.6 |
| n-hexyl acrylate | 10.0 |
| ethylene glycol dimethacrylate | 0.35 |
| 2,2'-azobis (2,4-dimethylpentanenitrile) | 0.05 |
| 2,2'-azobis(2-methylbutanenitrile) | 0.05 |

The cure temperature cycle used was as follows:
heat from 25° C. to 50° C. in 30minutes;
maintain at 50° C. for 5 hours;
heat from 50° C. to 90° C. in 4 hours;
maintain at 90° C. for 1 hour; and
cool from 90° C. to 25° C. in 6 hours.

The post-cure temperature cycle used was as follows:
heat from 25° C. to 120° C. in 3 hours;
maintain at 120° C. for 2 hours; and
cool from 120° C. to 25° C. in 3 hours.

The homopolymers of the 2-phenoxyethyl acrylate component have an optical refractive index of about 1.56, and are relatively rigid. For example, while a one cm diameter rod of such a homopolymer was somewhat rubbery, when this rod was bent into a U-shape, it cracked at the base of the U. Homopolymers of n-hexyl acrylate have a glass transition temperature of −58° C.

The resulting copolymer had a refractive index of 1.5365. A one cm diameter rod of this copolymer was folded 180° with no cracking and returned to its original shape within a few seconds.

EXAMPLE 2

Using conventional techniques, an IOL is formed including an optic made from the copolymer produced in Example 1 and haptics made of polypropylene filaments. In order to produce a 20 diopter, plano-convex optic, having a 0.305 mm edge thickness and a 6.0 mm diameter, the optic center thickness is approximately 0.76 mm. This represents a substantial improvement relative to the same type of lens made from a material having a refractive index of 1.46, such as certain silicone materials. Using a silicone material having a refractive index of 1.46, the center thickness of the optic is about 1.08 mm. This silicone optic, because of its relatively high center thickness, is more difficult to fold relative to the optic made of the copolymer produced in Example 1.

EXAMPLE 3

An IOL is produced having an optic as indicated in Example 2. Two substantially opposing haptics, such as shown in FIGS. 1 and 2, made from polypropylene filaments are bonded to this optic. The resulting IOL is inserted into the eye through a 3 mm surgical incision. In order to accomplish such insertion, the IOL is folded. Upon being released into the eye, the IOL regains its original shape in less than one minute and is fixed in position in the eye. After normal healing, the IOL is effective and useful in the eye as a replacement for the natural lens normally present in the eye.

EXAMPLE 4

The following formulation was blended, purged with nitrogen for 3 minutes and then cured into a crosslinked polymer.

|  | Weight % |
| --- | --- |
| 2-phenoxyethyl acrylate | 89.3 |
| n-hexyl acrylate | 5 |
| n-vinyl pyrrolidone | 5 |
| ethylene glycol dimethacrylate | 0.35 |
| 2,2'-azobis (2,4-dimethylpentanenitrile) | 0.05 |
| 2,2'-azobis (2-methylbutanenitrile) | 0.05 |
| UV light absorbing component[1] | 0.25 |

[1] 2-(2'-hydroxy-3'-t-butyl-5'-vinylphenyl)-5-chloro-2H-benzotriazole.

The cure and post-cure temperature cycles used were as described in Example 1.

The resulting copolymer had a refractive index of about 1.55, and was less tacky than the copolymer produced in Example 1. This copolymer had a tensile strength of 762±74 psi; an elongation at break of 143±61 percent; and a modulus of 422±70 psi. A one cm diameter rod of this copolymer was folded 180° with no cracking and returned to its original shape within a few seconds.

EXAMPLE 5

Using conventional techniques, an IOL is formed including an optic made from the copolymer produced in Example 4 and haptics made of polypropylene filaments. This IOL has a configuration substantially as shown in FIGS. 1 and 2.

The resulting IOL is inserted into the eye through a 3 mm surgical incision. In order to accomplish such insertion, the IOL is folded. Upon being released into the eye, the IOL regains its original shape in less than 1 minute and is fixed in position in the eye. After normal healing, the IOL is effective and useful in the eye as a replacement for the natural lens normally present in the eye.

while this invention has been described with respect to various specific examples and embodiments, it is to be understood that the invention is not limited thereto and that it can be variously practiced within the scope of the following claims.

What is claimed is:

1. A composition comprising a copolymer including a first constituent derived from a first monomeric component the homopolymers of which have a refractive index of at least about 1.50, said first monomeric component including one or more aryl-containing groups, a second constituent derived from a second monomeric component other than said first monomeric component the homopolymers of which have a glass transition temperature of less than about 30° C., and a third constituent derived from a crosslinking monomeric component in an amount effective to facilitate returning a deformed intraocular lens made of said composition to its original shape.

2. The composition of claim 1 wherein the homopolymers of said fist monomeric component have a substantial degree of rigidity and the homopolymers of said second monomeric component have a glass transition temperature of less than about 22° C.

3. The composition of claim 1 wherein said copolymer is optically clear and has a refractive index of at least about 1.50.

4. The composition of claim 1 wherein said first constituent is a major amount of said copolymer, and said first constituent and said second constituent together are at least about 80% by weight of said copolymer.

5. The composition of claim 1 wherein neither said second monomeric component nor said third monomeric component include any aryl-containing groups.

6. The composition of claim 1 wherein said copolymer further includes a fourth constituent derived from a hydrophilic monomeric component other than said first, second and third monomeric components, said fourth constituent being present in an amount effective to reduce the tackiness of said copolymer relative to a substantially identical copolymer without said fourth constituent.

7. The composition of claim 1 wherein each of said first, second and third monomeric components includes at least one functional group containing carbon-carbon unsaturation.

8. The composition of claim 1 wherein each of said first, second and third monomeric components includes at least one functional group containing a carbon-carbon double bond.

9. The composition of claim 1 wherein said first monomeric component is selected from the group consisting of styrene, vinyl carbazole, vinyl naphthalene, benzyl acrylate, phenyl acrylate, naphthyl acrylate, pentabromophenyl acrylate, 2-phenoxyethyl acrylate, 2-phenoxyethyl methacrylate, and mixtures thereof, and said second monomeric component is selected from the group consisting of n-butyl acrylate, n-hexyl acrylate, 2-ethylhexyl acrylate, 2-ethoxyethyl acrylate, 2,3-dibromopropyl acrylate, n-1, 1-dihydroperfluorobutyl acrylate and mixtures thereof.

10. The composition of claim 1 wherein said first constituent is a major amount by weight of said copolymer.

11. The composition of claim 6 wherein said hydrophilic monomeric component is selected from the group consisting of N-vinyl pyrrolidone, hydroxyalkyl acrylates, hydroxyalkyl methacrylates, acrylamide, N-alkyl acrylamides and mixtures thereof.

12. The composition of claim 6 wherein said copolymer is optically clear and has a refractive index of at least about 1.50.

13. The composition of claim 6 wherein said first constituent is a major amount of weight of said copolymer.

14. The composition of claim 6 wherein neither said second monomeric component nor said third monomeric component include any aryl-containing groups.

15. A composition comprising a copolymer including a first constituent derived from a first monomeric component the homopolymers of which have a refractive index of at least bout 1.50, said first monomeric component being selected from the group consisting of styrene, vinyl carbazole, vinyl naphthalene, benzyl acrylate, phenyl acrylate, naphthyl acrylate, pentabromophenyl acrylate, 2-phenoxyethyl acrylate, 2-phenoxyethyl methacrylate, 2,3-dibromopropyl acrylate and mixtures thereof, a second constituent derived from a second monomeric component other than said first monomeric component the homopolymers of which have a glass transition temperature of less than about 22° C., and a third constituent derived from a crosslinking monomeric component in an amount effective to facilitate returning a deformed intraocular lens made of said copolymer to its original shape.

16. The composition of claim 15 wherein said second monomeric component is selected from the group consisting of n-butyl acrylate, n-hexyl acrylate, 2-ethylhexyl acrylate, 2-ethoxyethyl acrylate, 2,3-dibromopropyl acrylate, and mixtures thereof.

17. The composition of claim 15 wherein said copolymer further includes a fourth constituent derived from a hydrophilic monomeric component other than said first, second and third monomeric components, said fourth constituent being present in a amount effective to reduce the tackiness of said copolymer relative to a substantially identical copolymer without said further constituent.

18. A composition comprising a copolymer including a first constituent derived from a first monomeric component the homopolymers of which have a refractive index of at least about 1.50, a second constituent derived from a second monomeric component other than said fist monomeric component the homopolymer of which have glass transition temperature of less than about 22° C., said second monomeric component is selected from the group consisting of n-butyl acrylate, n-hexyl acrylate, 2-ethylhexyl acrylate, 2-ethoxyethyl acrylate, 2,3-dibromopropyl acrylate and mixtures thereof, and a third constituent derived from a crosslinking monomeric component in an amount effective to facilitate returning a deformed intraocular lens made of said copolymer to its original shape.

19. The composition of claim 18 wherein said copolymer further includes a fourth constituent derived from a hydrophilic monomeric component other than said first, second and third monomeric components, said fourth constituent being present in an amount effective to reduce the tackiness of said copolymer relative to a substantially identical copolymer without said further constituent.

* * * * *